United States Patent [19]

Neville, Jr. et al.

[11] Patent Number: 4,520,011

[45] Date of Patent: May 28, 1985

[54] INACTIVATING PROTEIN SYNTHESIS BY INCUBATING ANTI-THY 1.1-RICIN A CHAIN MONOCLONAL ANTIBODY HYBRIDS WITH TARGET PROTEIN CELLS

[75] Inventors: David M. Neville, Jr., Bethesda; Richard J. Youle, Kensington, both of Md.

[73] Assignee: The United States of America as represented by the Department of Health and Human Services, Washington, D.C.

[21] Appl. No.: 350,222

[22] Filed: Feb. 19, 1982

[51] Int. Cl.[3] .................. A61K 39/44; A61K 39/395; A61K 45/05

[52] U.S. Cl. .......................................... 424/85; 514/8

[58] Field of Search .................... 424/85, 86, 89, 177; 435/172, 240, 241, 948; 436/548

[56] References Cited

U.S. PATENT DOCUMENTS

| | | | |
|---|---|---|---|
| 4,356,117 | 10/1982 | Neville et al. | 260/112 R |
| 4,359,457 | 11/1982 | Neville, Jr. et al. | 424/88 |
| 4,397,843 | 8/1983 | Neville et al. | 424/177 |

OTHER PUBLICATIONS

Youle et al., Proc. Natl. Acad. Sci., U.S.A., vol. 77, No. 9, pp. 5483–5486 (1980).
Masuho et al., Biochem. Biophys. Res. Comm., 90: 320–326 (1979).

Neville/Youle, *Immunology Reviews*, vol. 62, p. 135, 1981.

Vallera et al., "Bone Marrow Transplantation Across Major Histocompatibility Barriers".

*Primary Examiner*—Shep K. Rose
*Attorney, Agent, or Firm*—John S. Roberts, Jr.

[57] ABSTRACT

The rate of protein synthesis inhibition is significantly increased by adding excess ricin B chain to target cells independent of the amount of ricin A chain bound to the cell surface membrane. Ricin is a known toxin from albumin of the castor oil bean and contains an A chain and a B chain for binding to receptors. The present invention is concerned with ricin hybrids such as OX-7-ricin A chain and 19E12-F(ab) ricin A chain which were produced by conjugation of the ricin A chains with anti-Thy 1.1 monoclonal antibodies. The conjugates were utilized in pharmaceutical amounts in mice.

2 Claims, 1 Drawing Figure

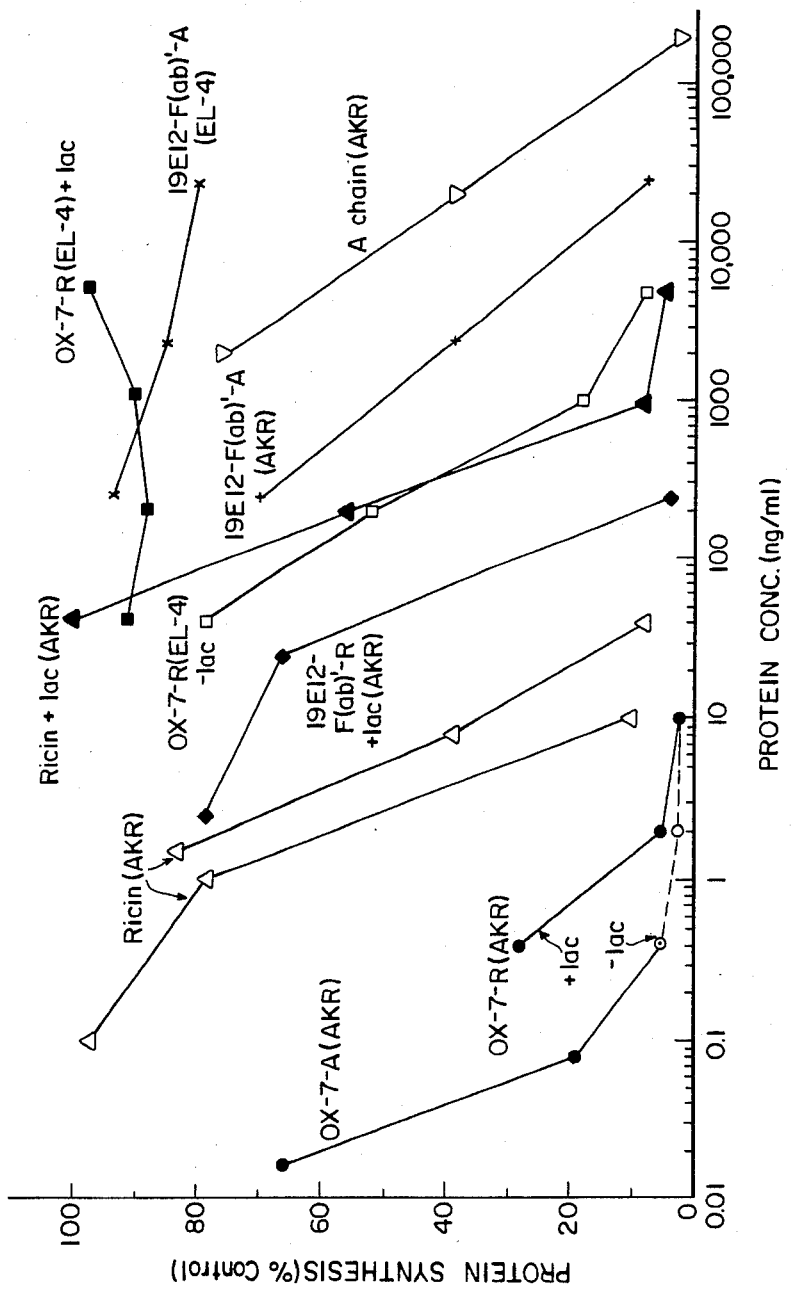

INACTIVATING PROTEIN SYNTHESIS BY INCUBATING ANTI-THY 1.1-RICIN A CHAIN MONOCLONAL ANTIBODY HYBRIDS WITH TARGET PROTEIN CELLS

BACKGROUND

Differences exist within the literature as to what constitutes the important variables in the design of hybrid toxins with altered receptor specificity. As originally conceived, the binding chain (B chain) of diphtheria toxin or ricin was replaced with an alternate binding protein modified to form a disulfide linkage with the toxin A chain. The theoretical advantage of this scheme was that toxin A chains have undetectable binding to cell membranes, and therefore the specificity of the hybrid would be directed entirely by the new binding moiety. Initial results with both diphtheria toxin and ricin A chain hybrids of peptide hormones were disappointing; under conditions which tested selectivity between target and non-target cells, potency of the hybrid relative to the parent toxin was markedly reduced. Certain antibody-toxin A chain hybrids showed good selectivity but were still less toxic than the parent toxin.

Subsequent discoveries showed the feasibility of altering the receptor specificity of intact toxins such as ricin by attaching a new binding moiety and inhibiting the usual ricin entry route by competition with lactose; U.S. Ser. No. 186,735 filed Sept. 12, 1980; U.S. Ser. No. 199,781 filed Oct. 23, 1980; and U.S. Ser. No. 341,572 filed Jan. 21, 1982. These hybrids in the presence of lactose were as toxic as ricin in the absence of lactose when assayed after a three-hour exposure to cells. These hybrids required a functional galactose binding site on the ricin B chain for optimal specific toxicity. Recently, however, several A chain hybrids have been reported which show a high degree of selectivity and are as potent as the parent toxins when assayed after 18-26 hours in tissue culture.

The present invention shows the rates of inactivation of protein synthesis between 2 and 24 hours for two A chain hybrids with widely differing affinities for the alternate receptor. The alternate binding proteins are monoclonal antibodies which bind the Thy 1.1 antigen present on AKR cells. Ricin B chain properties are studied by adding the B chain to mixtures of the A chain hybrids and target cells.

The protein inhibition rate is much lower for Thy 1.1 ricin A chain hybrid than for ricin alone. Additionally, the rate of inhibition by the hybrid can be increased by adding excess ricin B chain with no change in the amount of A chain bound to the target cells. In other words, ricin B chain facilitates entry of the A chain into the cytosol compartment of the cell by a process independent of the amount of A chain bound to the surface membrane.

PRIOR ART

Neville, D. M., and R. Youle, Monoclonal Antibody-Ricin or Antibody-Ricin A Chain Hybrids: Kinetic Analysis of Cell Killing for Tumor Therapy, *Immunology Reviews*, Vol. 62, p 135, (1981).

Roitt, Ivan, *Essential Immunology*, 4th Edition, Boston, Mass.: Blackwell Scientific Publications, 1980.

Youle, R. J., and D. M. Neville, Jr., Anti-Thy-1.2 Monoclonal Antibody Linked to Ricin is a Potent Cell Type Specific Toxin, *Proc. National Academy of Science, USA*, Vol. 77, p 5483 (1980).

Youle, R. J., G. T. Murray, and D. M. Neville, Jr., Studies on the Galactose Binding Site of Ricin and the Hybrid Toxin Man-6P-Ricin, *Cell*, Vol. 23, p. 551 (1981).

Vallera, Daniel A., Richad J. Youle, David M. Neville, Jr., John H. Kersey, Bone Marrow Transplantation Across Major Histocompatibility Barriers, (in press).

U.S. Pat. No. 4,359,459 (Neville et al.), Anti-Thy 1.2 Monoclonal Antibody-Ricin Hybrid Utilized as a Tumor Suppressant.

U.S. Pat. No. 4,356,117 (Neville et al.), Chemical Modifications of Proteins Which Induce New Receptor Specificities and Therefore Elicit New Effects in Cells.

U.S. Pat. No. 4,397,843 (Neville et al.), Ricin and Modeccin Reagents Effective as Tumor Suppressive Cytotoxic reagents (cip of Ser. No. 199,781 filed Oct. 23, 1980).

UTILITY STATEMENT

A method of utilizing protein target cells by mammalian cells which contain Thy 1.1 antigen receptor sites. This is accomplished by incubating anti-Thy 1.1-ricin A chain hybrids with target protein cells, such as AKR mouse thymocytes and separately adding ricin B chain to the mixture. The tumor suppressive cytotoxic effect is measured by normal pharmacological tests.

METHODS AND MATERIAL

Ricin, known in the literature, was prepared as has been previously reported in patent applications Ser. No. 199,781 (filed Oct. 23, 1980) and Ser. No. 186,735 (filed Sept. 12, 1980).

Ricin B chain was prepared from ricin by the method of Olsnes and Pihl (*Biochemistry*, Vol. 12, pp. 3121-3126, 1973), as modified by Cawley et al (*Arch. Biochem. Biophys.*, Vol. 190, pp. 744-755, 1973).

Ricin A chain was purified from ricin by the method of Cawley et al, *Cell*, 22:563-570, 1980.

Anti-Thy 1.1 monoclonal antibody, OX-7 was purchased from Accurate Chemical and Scientific Co., Westburg, NY and Anti-Thy 1.1 monoclonal antibody 19E12 was obtained from hybridoma cells provided by R. C. Nowinski, grown as acites in mice and purified over protein A Sepharose. F(ab)$_2$ was prepared as described in Nisonoff et al, *Nature*, 189:293-295 (1961). AKR-SL2 cells were also given by R. C. Nowinski. These hybridoma cells and AKR-SL2 cells are available to scientific researchers on request.

Hybrid Synthesis. OX-7-ricin A chain and 19E12-F(ab)'-ricin A chain were synthesized with N-succinimidyl(4-azidophenyldithio)propionate (SPDP) as follows. OX-7 IgG, 1.55 mg in 250 μl, was mixed with 10 μl of 4 mM SPDP in ethanol and incubated at room temperature 30 min. Then 10 μl of 0.625 M DTT in 5.1 M sodium acetate pH 4.7 was added to the IgG for 30 min. The mixture was passed over a 0.75 cm×5 cm G25F column and the IgG was pooled. To the IgG, 40 ul of 0.1 M 5,5'-dithiobis(2-nitrobenzoic acid (DTNB) in 0.78 M sodium borate pH 8.5 and 1.25 mM EDTA, was added. After 60 min. the IgG was freed from excess DTNB by passing over G25F in 0.4 M sodium borate pH 8.0 and this was added to 0.76 mg of freshly reduced ricin A chain in 0.5 ml and incubated at room temperature for 3 hrs and then dialyzed against PBS. Approximately fifty percent of the IgG was linked to ricin A chain and the hybrid mixture was used as such without further purification. 19E12-F(ab')$_2$, 9.6 mg in 2 ml, was incubated with 200 μl of 1 M DTT for 30 min. then passed over a 1.8 cm×18 cm G25F column. F(ab)' was pooled and mixed with 320 μl of 0.1 M DTNB in 0.78 sodium borate pH 8.5 and 1.25 mM EDTA for 30 min. The F(ab)' solution was passed over a 1.8 cm×18 cm G25F column and the F(ab)' was mixed with 6.5 mg of freshly reduced ricin A chain. The mixture was incubated at room temperature for 3 hrs then dialyzed against PBS. The hybrid was purified from unreacted ricin A chain by HPLC as described by Youle and Neville, *Proc. Natl. Acad. Sci.*, 77:5483–5486 (1980).

RESULTS AND DISCUSSION

Ricin A Chain Hybrids. Ricin, the ricin A chain, or a variety of hybrids formed between these two toxins and anti-Thy 1.1 monoclonal antibodies were incubated with murine lymphoma cells for 20 hours and their effect on protein synthesis was determined (see the Figure). The least toxic hybrid, the ricin A chain disulfide linked to the F(ab)' fragment of 19E12 IgG, (19E12-F(ab)'-A) was 7-fold more toxic than ricin A chain on Thy 1.1 expressing AKR cells.

Ricin Hybrids (the hybrid formed with ricin and the F(ab)' fragment of the low affinity antibody 19E12, 19E12-F(ab)'-R). After 20 hrs in the presence of 50 mM lactose (which partially blocks the ricin entry route), the hybrid formed with ricin and 19E12-F(ab)' is 5 times more toxic than ricin plus 50 mM lactose (see the Figure). The rate of protein synthesis inactivation for 200 ng/ml 19E12-F(ab)'-ricin in the presence of lactose is 14-fold faster than 200 ng/ml ricin in the presence of lactose. The FIGURE shows that 240 ng/ml 19E12-F(ab)'-A chain has little toxicity after 20 hrs. The B chain of ricin causes the enhancement of the Thy 1.1 specific entry rate.

Lactose has a definite effect on reducing the toxicity towards the target cells; however, the hybrid is still $10^3$ times more toxic than ricin plus lactose and $10^4$ fold more toxic to Thy 1.1 AKR cells than to non-target Thy 1.2 EL-4 cells (the Figure). Comparing the rate of inactivation of OX-7-ricin with that of OX-7-A at saturation, it would appear that the presence of the B chain has a relatively small effect. It is possible that the enhancement of entry rate produced by the B chain in low affinity ricin hybrids or when added to high affinity A chain hybrids is not operative for OX-7-ricin as a result of some interplay between the very tight binding to the Thy 1.1 receptor and the noncleavable character of the thioether linkage between ricin and OX-7 IgC.

Ricin A Chain Hybrids Plus Ricin B Chain. The effect of the ricin B chain on enhancing protein synthesis inactivation rates can be demonstrated when B chain is added to mixtures of OX-7-A and target cells. The enhancement of the inactivation slopes is 2-fold for the addition of 170 ng/ml of B and 5-fold for the addition of 1700 ng/ml of B. The maximum effect of ricin B does not seem to have been reached. The target cell specificity in the presence of B is maintained. No toxicity could be detected on EL-4 cells or on AKR cells in the presence of 10 ug/ml of competing OX-7 antibody for 35 ng/ml of OX-7-A plus 1700 ng/ml of B chain. The addition of B chain to high affinity ricin A chain hybrids is a way to increase the entry rate of the A chain without unduly sacrificing target cell specificity.

In the presence of 1700 ng/ml of B chain, OX-7-A toxicity still saturates at 176 ng/ml of OX-7-A. This indicates that the B chain only facilitates entry of A chain bound specifically to the Thy 1.1 antigen. To show that the ricin B chain increased the rate of A chain passage to the cytosol without increasing the number of A chains bound to the cell, OX-7-A chain above saturation was incubated with two series of cells for 1 hour. To one series OX-7-A chain remained in the medium and the incubation was continued for 3 hrs; then the rate of protein synthesis was determined. To another set the medium containing OX-7-A chain was removed and replaced with fresh medium lacing OX-7-A chain but containing ricin B chain. In these washed wells, the total amount of OX-7-A chain in the well equals the amount of OX-7-A chain bound to cells in the unwashed wells. Ricin B chain added to the washed cells accelerated the protein synthesis inactivation.

Although OX-7-A exhibits first order inactivation kinetics over 20 hours, OX-7-A is not required in the medium past 2 hours. Saturating OX-7-A chain was added to cells for 2 hours and replaced with fresh media lacking OX-7-A chain for 18 hours. The final rate of protein synthesis was essentially as low as in cells incubated with the same amount of OX-7-A chain over the whole 20 hours (Table 1 below). The OX-7-A chain inhibits protein synthesis only to 80% after 2 hours, thus prebound hybrid continues to inactivate protein synthesis over the 20 hours time course.

It should be pointed out that there is a major difference in the transport process between ricin, which exhibits a dose dependent lag period, and OX-7-A or OX-7-A plus B chain which show no detectable lag. OX-7-ricin at low doses sometimes displays a lag but always less than ricin for similar rates of inactivation of protein synthesis.

The high affinity A chain hybrid shows selectivity in dose response curves at 24 hours relative to a chain alone or to the non-target EL-4 cells of $10^5$, yet target cell killing is not greater than 99%, a fact due to the relative low rate of entry of the A chain into the cytosol via the Thy 1.1 receptor. Killing rates are limited by the number of occupied receptors and the efficiency of the entry process. Entry efficiency can be increased by the presence of the ricin B chain.

EXAMPLE 1

Super-saturated OX-7-A chain was incubated with two series of cells for one hour. To one series, OX-7-A chain remained in the medium and the incubation was continued for 3 hours after which the rate of protein synthesis was determined. To the other series, the medium containing OX-7-A chain was removed and replaced with fresh medium lacking OX-7-A chain, but containing ricin B chain. By replacing the medium in these wells, the total amount of OX-7-A chain in the well equals the amount of OX-7-A chain bound to cells in the unwashed wells. Ricin B chain added to the washed wells accelerated protein synthesis inactivation beyond that in unwashed wells without ricin B (Table 1). This shows that ricin B increases the rate of A chain passage to the cytosol without increasing the number of A chains bound to the cell.

EXAMPLE 2

AKR tumor cells, in 0.1 ml medium, were first incubated as noted in column 1, Table 1. They were then aspirated, placed in fresh medium, and incubated as noted in column 2. [$^{14}$C]leucine was added to the cells for 1.5 hours, then the cells were harvested and their protein synthesis rate determined, as noted in column 3.

TABLE 1

| Addition to AKR Cells | Addition to AKR Cells | Relative Rate of Protein Synthesis |
|---|---|---|
| (1 hr incubation) | (1 hr incubation) | |
| None | None | 100 |
| 880 ng/ml OX-7-A Chain | 880 ng/ml OX-7-A Chain | 73 |
| 880 ng/ml OX-7-A Chain | 1.2 μg/ml Ricin B | 49 |
| 880 ng/ml OX-7-A Chain | 12 μg/ml Ricin B | 29 |
| None | 12 μg/ml Ricin B | 100 |
| 2 hr incubation | 2 hr incubation | |
| None | None | 100 |
| 200 ng/ml OX-7-A Chain | 200 ng/ml OX-7-A Chain | 5 |

TABLE 1-continued

| Addition to AKR Cells | Addition to AKR Cells | Relative Rate of Protein Synthesis |
|---|---|---|
| 200 ng/ml OX-7-A Chain | None | 6 |
| 200 ng/ml OX-7-A Chain | 1.5 μg/ml Ricin B | 2 |
| None | 1.5 μg/ml Ricin B | 107 |

We claim:

1. In a method of inactivating protein synthesis in mammalian cells containing Thy 1.1 antigen receptor sites by incubating anti-Thy 1.1-ricin A chain monoclonal antibody hybrids with target cells in solution, the improvement which consists of the step of separately adding ricin B chain to the mixture.

2. In a method of making a tumor suppressive cytotoxic reagent composition active on AKR mouse thymocytes consisting essentially of a saturing amount of monoclonal antibody hybrid anti-Thy 1.1-ricin A chain, the improvement consisting of adding excess ricin-B chain.

* * * * *